United States Patent [19]

Inui et al.

[11] Patent Number: 4,611,591
[45] Date of Patent: Sep. 16, 1986

[54] EXPIRATION VALVE CONTROL FOR AUTOMATIC RESPIRATOR

[75] Inventors: Koichi Inui, Higashiosaka; Hiroshi Makita, Nara, both of Japan

[73] Assignee: Sharp Kabushiki Kaisha, Osaka, Japan

[21] Appl. No.: 751,083

[22] Filed: Jul. 2, 1985

[30] Foreign Application Priority Data

Jul. 10, 1984 [JP] Japan .......................... 59-104955[U]
Jul. 10, 1984 [JP] Japan .......................... 59-104956[U]

[51] Int. Cl.$^4$ ............................................. A62B 9/02
[52] U.S. Cl. ........................... 128/205.24; 128/204.21
[58] Field of Search ...................... 128/204.21, 204.23, 128/205.24; 137/315, 487.5, 488

[56] References Cited

U.S. PATENT DOCUMENTS 3,383,484  5/1968  Arp et al. ................... 128/204.23 X
4,333,452  6/1982  Au ............................... 128/205.24
4,393,869  7/1983  Boyarsky et al. .......... 128/204.23 X
4,527,557  7/1985  Devries et al. ................ 128/204.23

Primary Examiner—Stephen F. Husar
Attorney, Agent, or Firm—Flehr, Hohbach, Test, Albritton & Herbert

[57] ABSTRACT

An expiration valve for an automatic respirator comprises a main body which is separable into a valve body and a diaphragm and a container which engages to a tube for supplying control pressure to one side of the diaphragm. A means for controlling such an expiration valve comprises a means for generating pressure for opening and closing the valve, a means for controlling this pressure, a pressure detector means, an exhaust means and a control means so that the valve can be electronically controlled for both the valve opening/closing functions and for the positive end expiratory pressure function.

5 Claims, 7 Drawing Figures

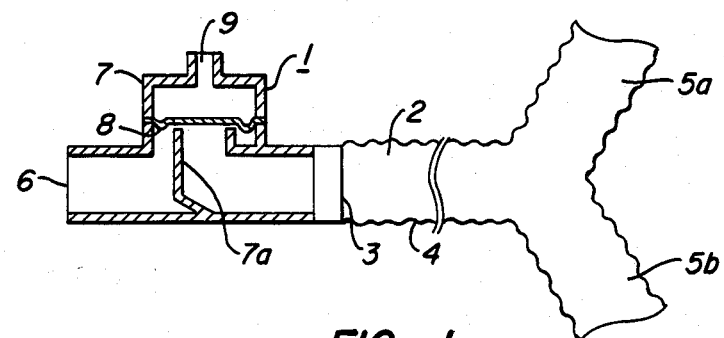
FIG._1.
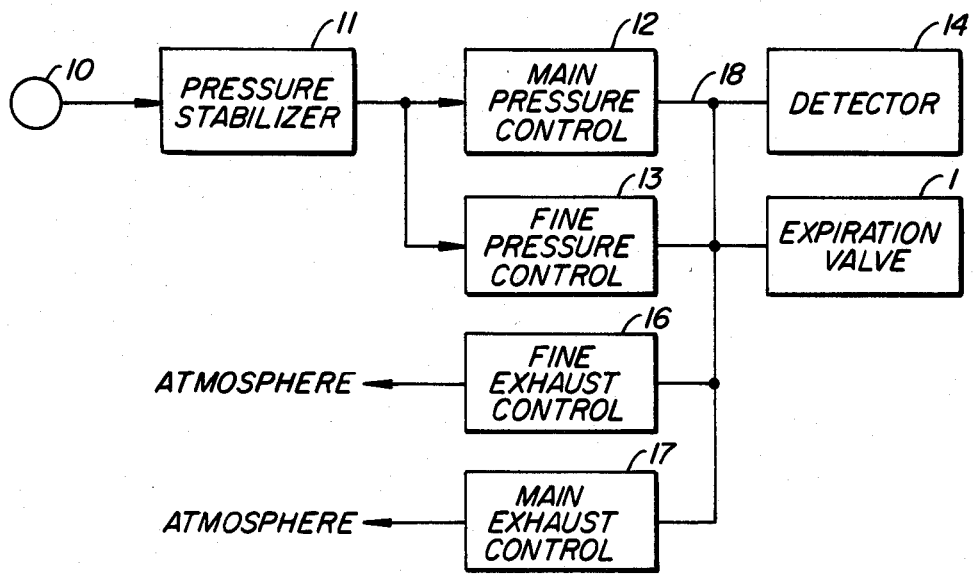
FIG._2.
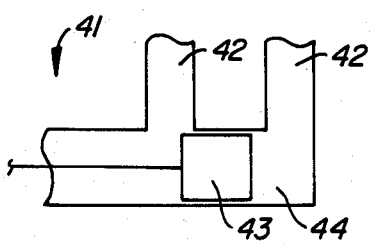
FIG._4. PRIOR ART
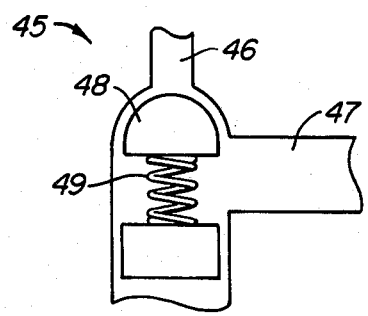
FIG._5. PRIOR ART
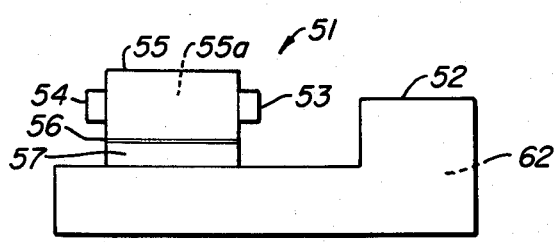
FIG._6.
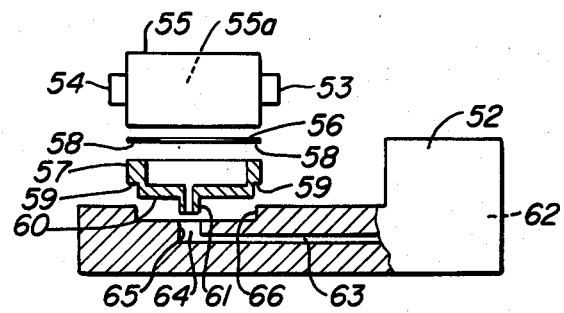
FIG._7.

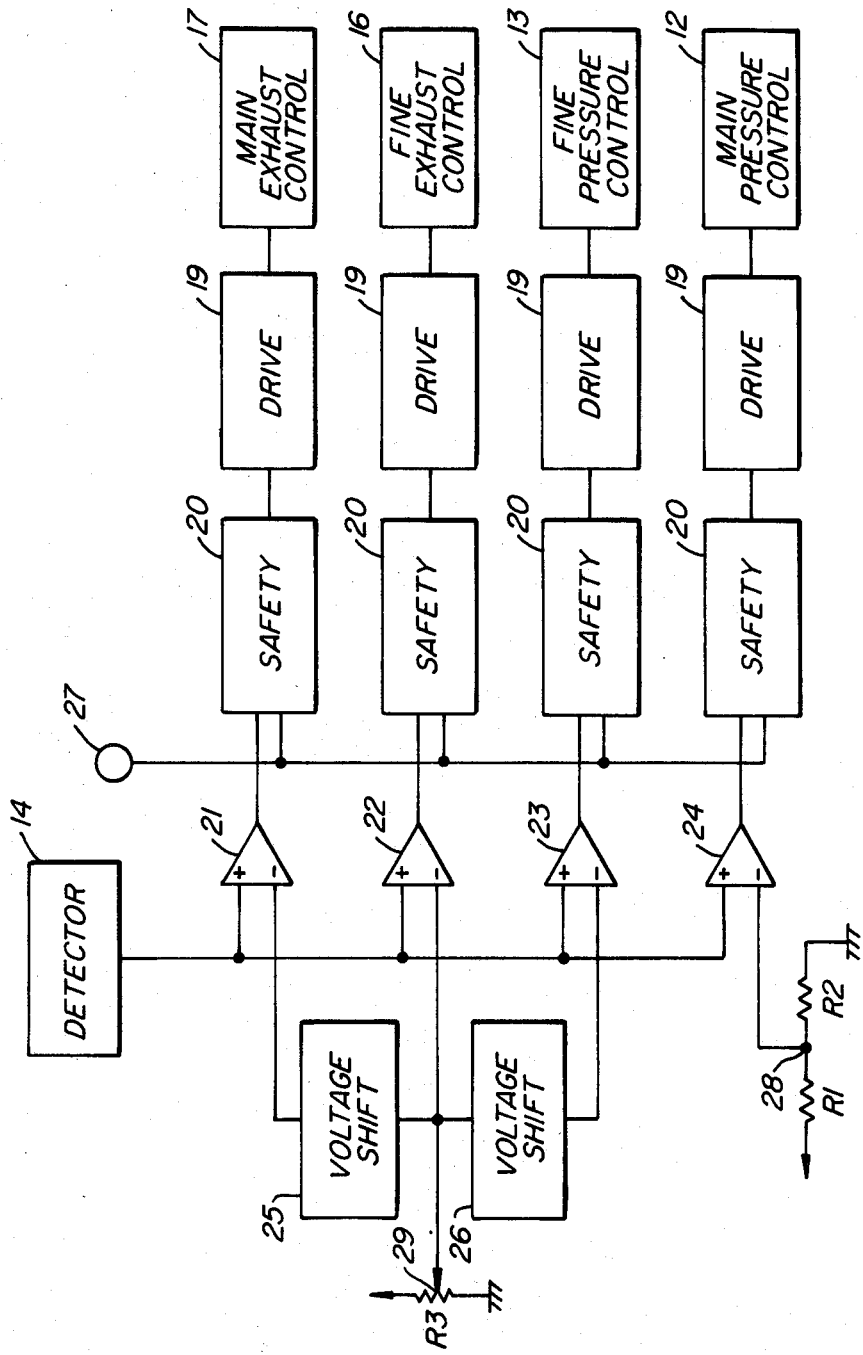
FIG._3.

EXPIRATION VALVE CONTROL FOR AUTOMATIC RESPIRATOR

This invention relates to a control means for an expiration valve installed in the expiration circuit of an automatic respirator and more particularly to an expiration valve of the pressure control type applicable to a medical respirator.

The purpose of an automatic respirator is to help a patient to breathe. Its expiration circuit is for passing the gas breathed out of the patient and is provided with an expiration valve adapted to close at the time of inspiration and to open at the time of expiration.

An expiration valve of the pressure control type contains a diaphragm inside the valve housing. Closing and opening of the valve are controlled by applying an appropriate control pressure on this diaphragm. Such an expiration valve is generally installed on top of an apparatus for generating the control pressure, but if the expiration valve is assembled on such an apparatus, workability is severely affected because of the parts which are connected to the valve as well as the peripheral equipment. Moreover, the immediate vicinity of the diaphragm cannot be sterilized satisfactorily.

Recently, medical respirators are often adapted to increase the gas-exchange efficiency by using a breathing method called PEEP (Positive End Expiratory Pressure). Since the conventional type of expiration valve is adapted merely to open and close, however, a separate PEEP valve must be provided in order to add the PEEP function to a respirator. As shown IN FIGS. 4 and 5, respectively, the conventional expiration valve 41 is adapted to control the opening and closing of its expiration circuit 42 by the motion of a piston 43 inside a cylinder 44 and a typical PEEP valve 45 is provided at the branch point between the expiration circuit 46 and the exhaust circuit 47 and a valve head 48 is normally pressed upward in the direction of the expiration circuit 46 by a spring 49 with a certain pressure. Thus, since the conventional expiration valve is a mechanical device comprising a cylinder and a piston and the PEEP valve is also a mechanical valve making use of a spring means, it is difficult to control them electronically by using microcomputer or the like, Moreover, the expiration valve and the PEEP valve described above will have to be connected in series if both the opening-closing function of the former and the PEEP function are desired.

It is therefore an object of the present invention to provide an expiration valve to which the valve opening-closing function and/or the PEEP function can be given merely by controlling the pressure on the valve so that it can be operated electronically unlike the conventional mechanical valves.

It is another object of the present invention to provide an expiration valve of which all constituent parts can be disassembled and assembled somewhere away from a pressure generating device so that the assembly workability of the valve will be inproved and each part can be cleaned and sterilized.

The above and other objects of the present invention are achieved on the one hand by providing an expiration valve control unit adapted to control the opening and closing of an expiration valve by pressure. Such a unit comprises a control pressure generating device for generating such a control pressure, a pressure controlling means for controllably increasing the control pressure, a pressure detecting means for detecting the pressure, an exhaust means for exhausting gas and a control means for controlling the pressure controlling and exhaust means on the basis of the results detected by the pressure detecting means in such a way that pressure will be maintained at a predetermined level necessary for the opening/closing function and the PEEP function of the expiration valve. At the time of inspiration, the pressure controlling means operates and the control pressure increases until it become capable of closing the expiration valve. When this pressure is detected by the pressure detecting means, the pressure controlling means is closed. At the time of expiration, on the other hand, the exhaust means operates and the control pressure is released to the atmosphere. When the PEEP is applied, both the pressure controlling means and the exhaust means are operated so that PEEP will be obtained without releasing the pressure completely to the atmosphere.

On the other hand, the present invention provides an expiration valve having a main housing, a valve body and a diaphragm which are assembled together separately. The main body is connected to a lead tube through which the control pressure is supplied and a control pressure container for applying the control pressure to one side of the diaphragm is engagingly attached. After the valve body, the diaphragm and the control pressure container are assembled somewhere else to form the expiration valve, it is placed on top of the control pressure generating device and is connected to the lead tube. When it is desired to disconnect the expiration valve, the valve body, the diaphragm and the connecting container are removed from the tube as a unit and then the unit is disassembled into the constituent pieces.

FIG. 1 is a cross-sectional view of an expiration valve embodying the present invention.

FIG. 2 is a block diagram of a control system of the expiration valve of FIG. 1.

FIG. 3 is a block circuit diagram of the control system of FIG. 2.

FIG. 4 is a cross-sectional view schematically showing a conventional expiration valve.

FIG. 5 is a cross-sectional view schematically showing a conventional PEEP valve.

FIG. 6 is a frontal view of an expiration valve of the present invention assembled on top of a control pressure generating device.

FIG. 7 is a cross-sectional view showing the expiration valve of FIG. 6 when it is separated from the control pressure generating device.

FIG. 1 is a cross-sectional view of an expiration valve 1 according to one embodiment of the present invention installed in an expiration circuit 2. The entrance side 3 of this expiration circuit 2 is attached to a bellows-like hose 4. The other side of the hose 4 is split into two circuits, one of which 5a is connected to an inlet of the main housing of the respirator (not shown) and the other of which 5b is connected to the patient. The expiration valve 1 is adapted to control the gas motion between the entrance side 3 and the exit side 6 of the expiration circuit 2 and includes a valve body 7 and a diaphragm 8. A control pressure is adapted to be applied from the side of the top surface of the diaphragm 8 so as to press the bottom surface of the diaphragm against a valve piece 7a provided inside the valve body 7, thereby controlling the opening/closing function and the PEEP function of the valve piece. Numeral 9 in FIG. 1 indicates an inlet for the control pressure and is connected to a control pressure generating device (not shown).

FIG. 2 is a block diagram of a control system of the expiration valve of FIG. 1. A pressure source 10 generated by the aforementioned pressure generating device is connected to a pressure stabilizer 11 to stabilize the pressure. The stabilized pressure is transmitted to a main pressure control curcuit 12 and a fine pressure control circuit 13. At the time of inspiration, the main pressure control circuit 12 is opened to transmit pressure to a control pressure circuit 18. When this pressure reaches a level high enough to close the expiration valve 1, it is detected by the pressure detector 14, which closes the main pressure control circuit 12 as well as the expiration valve 1. During the inspiration period, the fine pressure control circuit 13, the fine exhaust control circuit 16 and the main exhaust control circuit 17 remain closed. At the time of expiration, on the other hand, the main exhaust control circuit 17 and the fine exhaust control circuit 16 are opened so that the control pressure circuit 18 becomes open to the atmosphere and the expiration valve 1 is opened. During the expiration period, the main pressure control circuit 12 and the fine pressure control circuit 13 remain closed.

If it is desired to apply the PEEP, the main exhaust control circuit 17 which has been open from the beginning of expiration is closed when the control pressure drops to a predetermined level which is set sufficiently higher than the desired PEEP pressure. Thereafter, only the fine exhaust control circuit 16 remains open until the pressure drops to the desired level. When a desired level is reached where the PEEP is generated, the fine exhaust control circuit is also closed.

Immediately after the start of an expiration period, the respiration circuit pressure may fluctuate significantly, depending on how the respirator is set. This may sometimes cause the control pressure to drop below the level where the desired PEEP is generated. In order to prevent such a situation, the system is adapted to open the fine pressure conrol circuit 13 when the control pressure drops below the level where the PEEP is generated so that the control pressure can be raised again. This system is also so adapted that if a pressure change during a PEEP control causes the control pressure to increase beyond the level where the PEEP is generated, the fine exhaust control circuit 16 is opened to lower the control pressure so that the desired PEEP can be obtained.

FIG. 3 is a block circuit diagram of the control system. When inspiration starts, the output "L" from a comparator 24 remains on the "L" level so that the main pressure control circuit 12 is opened. When the main pressure control circuit 12 is opened, the output from the pressure detector 40 becomes gradually larger. When this output reaches a reference voltage 28 determined by resistors R1 and R2, the output of the comparator 24 switches from "L" to "H" and the main pressure control circuit 12 is closed. In FIG. 3, numerals 19 and 20 indicate individually a driving circuit and a safety circuit, respectively. The safety circuits 20 are for ensuring the safety of the respirator and are controlled by an inspiration/expiration signal 27. In other words, since the main exhaust control circuit 17, the fine exhaust control circuit 16 and the fine pressure control circuit 30 must all be closed during an inspiration period, the inspiration/expiration signal 27 is applied through the safety circuits 20 to the outputs from the respective comparators. Since the main pressure control circuit 12 must be closed during an expiration period, it is made certain to be closed by the respective safety circuit 20 in a similar manner.

When it switches to an expiration period, the main exhaust control circuit 17 and the fine exhaust control circuit 16 are opened since the outputs from the comparators 21 and 22 remain on the level "H". When they are opened, applied pressure begins to drop. As soon as the output from the pressure detector 14 drops to a voltage level determined by a voltage shift circuit 25 somewhat higher thanthe PEEP-setting value 29 determined by the resistor R3, the level of the comparator 21 switches from "H" to "L" and the main exhaust control circuit 17 is closed. In this situation, only the fine exhaust control circuit 16 remains open and the control pressure continues to drop. When the output from the pressure detector 14 drops to the PEEP-setting value 29, the level of the comparator 22 switches from "H" to "L" and the fine exhaust control circuit 16, too, becomes closed. If a pressure fluctuation in the respirator circuit causes it to further drop from the PEEP-setting value 29 to a somewhat lower voltage value determined by the voltage shift circuit 26, the level of the comparator 23 switches from "H" to "L" and the fine pressure control circuit 13 is opened. In FIG. 2, the main pressure control circuit 12 and the main exhaust control circuit 17 may, for example, be composed of an electromagnetic valve while the fine pressure control circuit 13 and the fine exhaust control circuit 16 may each be a series connection of a variable resistor and an electromagnetic valve.

FIG. 6 shows an expiration valve 51 of the present invention as assembled on top of a control pressure generating device 52. The expiration valve 51 is adapted to control the gas motion between the entrance 53 and the exit 54 of the expiration circuit (not shown) and is composed of a valve body 55, a diaphragm 56 and a control pressure container 57 connected at the bottom, these constituent parts being separable. The entrance 53 is connected to the housing of the respirator (not shown) and the patient. The gas breathed out by the patient is adapted to be exhausted from the exit 54. There is a valve piece 55a inside the valve body 55. When the upper surface of the diaphragm 56 is pressed against the valve piece 55a, communication is cut off between the entrance 53 and the exit 54. When the upper surface of the diaphragm 56 is separated from the valve piece 55a, communication is restored between the entrance 53 and the exit 54. The diaphragm 56 is affixed with its edge section 58 sandwiched between the lower edge surface of the valve body 55 and the upper edge of the control pressure container 57. The control pressure container 57 is formed like a funnel with a step 59 provided on the external circumference near the middle. There is a tubular passage 61 protruding from the lower surface 60.

The control pressure generating device 52 is adapted to generate an appropriate control pressure in the control section 62. The control pressure is adapted to control the expiration valve 51 through the lead tube 63 laid horizontally inside the control pressure generating device 52. The end part 64 of the lead pipe 63 is bent upward to form an expiration valve attachment means 65. This attachment means 65 is also provided with an attachment opening 66 adapted to engage with the step 59.

In order to assemble the expiration valve 51 on top of the control pressure generating device 52, the valve body 55, the diaphragm 56 and the control pressure container 57 are assembled initially somewhere away and the assembly as a unit is placed on top of the control pressure generating device 52 so that the step 59 and the attachment opening 66 will match and that the tube 63 will engage with the tubular passage 61 of the control pressure container 57. Thereafter, the valve body 55 and the control pressure generating device 52 are affixed by an independent affixing means (not shown). When the expiration valve 51 is removed, the valve body 55, the diaphragm 56 and the connecting container 57 are removed as a single unit from the lead tube 63 and then the unit is disassembled into the constituent parts.

What is claimed is:

1. In an expiration valve control adapted to control an expiration valve installed in an expiration circuit of an automatic respirator, a control pressure generating means for generating a control pressure for controlling the opening and closing of an expiration value, a pressure control means for controllably increasing said control pressure, a pressure detector means for detecting said increased pressure, an exhaust control means for controllably releasing said increased pressure, and a control means for controlling said pressure control means and said exhaust control means on the basis of the result detected by said pressure detector means such that said increased pressure will be maintained at a predetermined pressure level.

2. The expiration valve control of claim 1 wherein said pressure control means includes a main pressure control circuit and a fine pressure control circuit which is connected in parallel with said main pressure control circuit.

3. The expiration valve control of claim 1 wherein said exhaust control means includes a main exhaust control circuit and a fine exhaust control circuit which is connected in parallel with said main exhaust control circuit.

4. The expiration valve control of claim 2 wherein said exhaust control means includes a main exhaust control circuit and a fine exhaust control circuit which is connected in parallel with said main exhaust control circuit.

5. In an expiration valve with a valve piece installed in an expiration circuit of an automatic respirator, said valve piece being adapted to be controlled for opening and closing by a control pressure supplied through a lead tube, a valve main body which is separable into a valve body and a diaphragm, and a control pressure container engaged to an end section of said lead tube, said control pressure container being adapted to connect said tube through to said valve main body and to apply said control pressure on one side of said diaphragm.

* * * * *